United States Patent [19]
Bretton

[11] Patent Number: 6,138,680
[45] Date of Patent: Oct. 31, 2000

[54] METHOD FOR DESTROYING RETINAL PIGMENT EPITHELIAL CELLS

[75] Inventor: Randolph H. Bretton, Maryland Heights, Mo.

[73] Assignee: Bausch & Lomb Surgical, Inc., Claremont, Calif.

[21] Appl. No.: 09/014,492

[22] Filed: Jan. 28, 1998

Related U.S. Application Data

[60] Provisional application No. 60/037,994, Feb. 13, 1997.

[51] Int. Cl.⁷ .......................... A61B 19/00; A01N 37/18; A01N 38/00; A01N 43/04
[52] U.S. Cl. .................................. 128/898; 514/2; 514/8; 514/1.2; 514/21; 514/23
[58] Field of Search ................................ 128/898; 514/2, 514/8, 12, 21, 23

[56] References Cited

U.S. PATENT DOCUMENTS 4,920,104  4/1990  DeVore et al. .............................. 514/54

OTHER PUBLICATIONS

Nagasaki et al (Progress in Retinal and Eye Res., 17:77–98), 1998.
Handa et al (Current Eye Res., 15:1039–1044), 1996.
Burgess et al (J. Cell Bio., 111:2129–2138), 1990.

*Primary Examiner*—Susan Ungar
*Attorney, Agent, or Firm*—Rita D. Vacca

[57] ABSTRACT

A method for destroying retinal pigment epithelial cells in an eye in order to prevent the occurrence of proliferative vitreoretinopathy. A solution containing a basement membrane binding agent conjugated to a cytotoxic agent is introduced into the vitreous chamber. The solution is maintained in the vitreous chamber for a period of time sufficient to permit the basement membrane binding agent to bind to basement membranes lining the vitreous chamber. The solution is then removed from the vitreous chamber, whereby a portion of the basement membrane binding agent remains bonded to basement membranes within the vitreous chamber, thereby exposing retinal pigment epithelial cells disposed on the basement membrane to the cytotoxic agent.

11 Claims, No Drawings

METHOD FOR DESTROYING RETINAL PIGMENT EPITHELIAL CELLS

This application claims benefit to provisional application No. 60/037,994, filed Feb. 13, 1997, now abandoned.

BACKGROUND OF THE INVENTION

The present invention relates to a method for destroying retinal pigment epithelial and like proliferative cells for the purpose of preventing the occurrence of proliferative vitreoretinopaty (PVR) or traction band formation following the current treatment for retinal tears and detachments. More particularly, the present invention is directed to a method for destroying retinal pigment epithelial and like proliferative cells on the retina surface in the vitreous chamber of the eye through the application of a membrane-binding agent having a toxin bonded thereto.

Proliferative vitreoretinopathy (PVR) is the most common cause of blindness after retinal detachment. In order to gain access to a torn or detached retina, an incision typically is made at the pars plana of the eye for the purpose of introducing a surgical instrument into the vitreous chamber of the eye. In the case of retinal tears and detachments, a vitrectomy procedure and reattachment of the retina is performed in which a torn or detached portion of the retina is reattached using a surgical laser instrument, cautery, adhesives or tamponades. Following retinal detachment or tears, proliferative cells such as but not limited to retinal pigment epithelial cells, glial cells, fibroblasts, macrophages, myofibroblast-like cells and the like are released into the vitreous chamber. These proliferative cells, thought to be primarily retinal pigment epithelial (RPE) cells and therefor hereinafter referred to collectively as RPE cells, then proliferate in the vitreous chamber. The proliferation of these cells in the vitreous chamber and on the retina, cause traction bands to form and re-detach the retina thus causing blindness. Accordingly, a method of preventing proliferative vitreoretinopathy is desired. A composition useful in the prevention of proliferative vitreoretinopathy is likewise desired.

SUMMARY OF THE INVENTION

The method of the present invention is used to destroy retinal pigment epithelial cells within the vitreous chamber of the eye following a retinal tear or detachment through the use of a basement membrane binding agent. A cytotoxic agent capable of destroying retinal pigment epithelial cells preferably is conjugated to the basement membrane binding agent. Following vitrectomy, if necessary, and retina reattachment, the basement membrane binding agent conjugated to the cytotoxic agent is introduced into the vitreous chamber of the eye. The basement membrane binding agent conjugated to the cytotoxic agent is allowed to remain in the vitreous chamber for a predetermined period of time sufficient to permit the basement membrane binding agent to bind to the basement membrane lining the vitreous chamber of the eye, and more specifically, the inner limiting membrane (ILM). Any excess material is then removed from the vitreous chamber. Retinal pigment epithelial cells released into the vitreous chamber and subsequently disposed on the basement membranes are thus exposed to the cytotoxic agent conjugated to the basement membrane binding agent, resulting in the destruction of the retinal pigment epithelial cells.

In an alternative embodiment of the method of the present invention preferably for use in aphakic eyes, a first basement membrane binding agent is introduced into the eye prior to performing a vitrectomy. The first basement membrane binding agent is allowed to remain in the eye for a predetermined period of time sufficient to permit the basement membrane binding agent to bind to the basement membranes within the eye. Excess of the first basement membrane binding agent is then removed from the eye. A vitrectomy, if necessary, and retina reattachment is then performed, thus exposing additional basement membranes within the vitreous chamber. A second basement membrane binding agent having a cytotoxic agent conjugated thereto is then introduced into the eye and permitted to remain therein for a period of time sufficient to permit the basement membrane binding agent to bind to the basement membranes within the vitreous chamber. Any excess material is then removed from the eye. Retinal pigment epithelial cells disposed on the basement membranes within the vitreous chamber are thus exposed to the cytotoxic agent conjugated to the second basement membrane binding agent, resulting in the destruction of the retinal pigment epithelial cells.

DETAILED DESCRIPTION

The method of the present invention is intended to destroy proliferative cells referred to herein collectively as retinal pigment epithelial cells disposed on the interior surfaces of the vitreous chamber of the eye. By destroying these cells, the cells can not proliferate and/or migrate along the surface of the retina and form the traction bands which are indicative of proliferative vitreoretinopathy (PVR) resulting in retinal detachment. The subject method thereby is capable of preventing the occurrence of proliferative vitreoretinopathy (PVR). The method of the present invention can be employed in connection with any retina reattachment procedure.

Vitrectomy and retina reattachment entails the formation of an incision through a surface of the eye in order to provide direct access to the internal vitreous chamber of the eye. Although the necessary incision is usually formed at the pars plana of the eye, it will be appreciated that alternative locations for this incision can be selected at the discretion of the surgeon. Following the formation of the incision, a vitrectomy is usually required and performed prior to introducing a cautery instrument through the incision into the vitreous chamber of the eye. The instrument usually a laser, is advanced through the vitreous chamber such that the laser or like suitable instrument is in direct contact with the retina surface of the eye. The retina is reattached through the use of the laser for cauterization thereof. Alternatively, the retina may be reattached using suitable adhesives and/or tamponades.

It has been discovered that certain agents will bind to basement membranes, including basement membranes within the vitreous chamber. The basement membrane binding agents, when bonded to the basement membrane or ILM of the vitreous chamber, are in direct contact with the retinal pigment epithelial cells during the progression of PVR. The method of the present invention is based upon observations of such cellular proliferation.

In a first embodiment of the method of the present invention, a solution containing a basement membrane binding agent is introduced into the vitreous chamber following vitrectomy if performed and retina reattachment. In this first embodiment of the present invention, a cytotoxic agent is conjugated to the basement membrane binding agent. As above-discussed, the basement membrane binding agent will bind to the basement membranes that form the interior surface of the vitreous chamber, thereby providing direct contact between retinal pigment epithelial cells and the cytotoxic agent conjugated to the basement membrane binding agent. The solution containing basement membrane binding agent conjugated to the cytotoxic agent is retained within the vitreous chamber for a predetermined period of time sufficient to permit the basement membrane binding agent to bind to the basement membranes within the vitreous chamber. It will be appreciated that the length of time required for binding the basement membrane binding agent to the basement membranes within the vitreous chamber will be dependent upon a number of factors, including, but not limited to, the concentration of the basement membrane binding agent in the solution that is introduced into the vitreous chamber. Excess of the solution containing the basement membrane binding agent conjugated to the cytotoxic agent is then removed from the vitreous chamber. A variety of techniques can be used for the removal of this solution, including known aspiration and irrigation/aspiration techniques.

Following removal of the excess solution containing the basement membrane binding agent from the vitreous chamber of the eye, a tamponade may or may not be applied and the incision in the eye is then closed to complete the procedure.

It will be appreciated that the basement membrane binding agent will remain bonded to the basement membranes within the vitreous chamber. The cytotoxic agent conjugated to the basement membrane binding agent will thus have direct access to the retinal pigment epithelial cells on the interior surface of the vitreous chamber. In particular, it will be appreciated that the retinal pigment epithelial cells will come into contact with the basement membrane binding agent as the retinal pigment epithelial cells attempt to proliferate and migrate across the interior surface of the vitreous chamber. The retinal pigment epithelial cells will internalize the cytotoxic agent, thereby resulting in the destruction of the retinal pigment epithelial cells on the interior surface of the vitreous chamber and thus preventing PVR and the resultant blindness.

In an aphakic eye, it should be noted that the anterior chamber of the eye is exposed to the vitreous chamber of the eye and also includes basement membranes, e.g., the corneal endothelium. Due to the fact that corneal endothelium will not regenerate once it has been damaged, particular care should be exercised to ensure that the solution containing the basement membrane binding agent conjugated to a cytotoxic agent does not come into contact with the corneal endothelium. A second embodiment of the present invention is intended to protect the corneal endothelium from the effects of the cytotoxic agent.

In the second embodiment of the method of the present invention, a first solution containing a basement membrane binding agent without a cytotoxic agent conjugated thereto is introduced into the eye prior to performing a vitrectomy and retina reattachment. The basement membrane binding agent in the first solution will bind to the exposed basement membranes within the eye, particularly the corneal endothelium. The first solution containing a basement membrane binding agent is allowed to remain in the eye for a predetermined period of time sufficient to ensure that adequate bonding has occurred between the first basement membrane binding agent and the basement membranes within the eye. The first solution containing a basement membrane binding agent is then removed from the eye using known aspiration or irrigation/aspiration methods as above-discussed with respect to the first embodiment of the present invention. A vitrectomy if necessary and retina reattachment procedure are then performed using known techniques.

A second solution containing a basement membrane binding agent conjugated to a cytotoxic agent is then introduced into the vitreous chamber. It is preferable that the second solution bind only to those basement membranes within the eye not previously bonded to the first basement membrane binding agent, thereby ensuring that the cytotoxic agent destroys retinal pigment epithelial cells within the vitreous chamber without damaging the corneal endothelia. For this reason, it is preferable that the first basement membrane binding agent be the same substance as the second basement membrane binding agent, thus ensuring that the first and second basement membrane binding agents bind to the same sites on the basement membranes.

Polylysine can be used as a basement membrane binding agent in connection with the method of the present invention. It will be appreciated that the molecular weight of polylysine or other polymeric basement membrane binding agents can be varied. This aspect of polymeric basement membrane binding agents makes then particularly beneficial when used in connection with the method of the present invention. In particular, it will be appreciated that the binding affinity of a polymeric basement membrane binding agent such as polylysine will increase as its molecular weight increases due to the increased number of binding sites available on the higher molecular weight molecule. Higher molecular weight polylysine molecules thus will tend to displace lower molecular weight polylysine molecules previously bonded to a basement membrane. For the above-discussed reasons, if a polymeric basement membrane binding agent such as polylysine is used in connection with the method of the present invention, it is preferable that the molecular weight of the first basement membrane binding agent be at least as great as the molecular weight of the second basement membrane binding agent in order to ensure that the second basement membrane binding agent does not displace the first basement membrane binding agent. In order to provide even greater assurances that the second basement membrane binding agent does not displace the first basement membrane binding agent, it is preferably that the molecular weight of the first basement membrane binding agent be greater than the molecular wight of the second basement membrane binding agent.

The second solution containing a basement membrane binding agent conjugated to a cytotoxic agent is retained within the vitreous chamber for a predetermined period of time sufficient to ensure that adequate bonding has occurred between the second basement membrane binding agent and the basement membranes not previously bonded to the first basement membrane binding agent. As above-discussed, the amount of time required is dependent upon a number of factors. Excess of the second solution is then removed from the eye using known techniques such as aspiration or irrigation/aspiration. For the reasons discussed above with respect to the first embodiment of the present invention, the cytotoxic agent will tend to destroy retinal pigment epithelial cells within the vitreous chamber, thereby preventing PVR.

In a third embodiment of the present invention, the above-described steps of the first embodiment of the invention are performed. Next, a second solution containing a second basement membrane binding agent is provided and is introduced into the eye for the purpose of displacing any of the first basement membrane binding agent that may have come into contact with the corneal endothelium. For the above-discussed reasons, it is preferable that the second basement membrane binding agent be the same substance as the first basement membrane binding agent. In addition, it is preferable that the molecular weight of the second basement membrane binding agent be greater than the molecular weight of the first basement membrane binding agent, thereby ensuring that the second basement membrane binding agent will displace the first basement membrane binding agent on the corneal endothelium.

A variety of basement membrane binding agents can be used in connection with the method of the present invention. In a preferred embodiment of the present invention polylysine is employed as a basement membrane binding agent. Poly-L-lysine has been shown to be effective when used in connection with the method of the present invention. It is possible that poly-D-lysine also can be effective. Polylysine is advantageously used in connection with the present invention due to its availability, relatively low cost, and its ability to be formulated in a variety of molecular weights. Other basement membrane binding agents believed to be useful in connection with the present invention includes, but are not limited to, fibronection, fibroblast growth factors, laminin, type IV collagen, perlecan, decorin, thrombospondin, tenascin, vitronection, heparin, heparan sulfate, poly-arginine, dextran, dextran sulfate, chondroitin sulfate, hyaluronic acid, platelet factor IV, fibrin, and fibrinogen.

A variety of known cytotoxic agents can be used in conjunction with the method of the present invention. In a preferred embodiment of the present invention, a ribosomal inhibitory protein such as saporin or ricin is used as the cytotoxin agent. Ribosomal inhibitory proteins are preferable due to the fact that they contain more inhibitory activity per microgram than other cytotoxic agents that can be used in connection with the method of the present invention. Other cytotoxic agents believed to be efficacious when used in connection with the method of the present invention include, but are not limited to, antimitotic drugs such as methotrexate, 5-fluorouracil, daunomycin, doxorubicin, mitoxanthrone, vinca alkaloids, vinblastine, colchicine, or cytochasins, when used as the cytotoxic agent. In addition, ionophores such as monesin and ouabain can be used as the cytotoxic agent in connection with the method of the present invention. It will be appreciated that antimitotic conjugates will destroy retinal pigment epithelial cells while exhibiting less toxicity to the iris and corneal endothelium compared to the ribosomal inhibitory proteins.

A variety of known methods can be employed for conjugating the cytotoxin to the basement membrane binding agent. For example, the carboxyl groups of the cytotoxic agent can be bonded to the amines of the basement membrane binding agent using a water-soluble carbodiimide technique. When this technique for conjugation is used, the entire conjugate will be internalized by the retinal pigment epithelial cells and the basement membrane binding agent will then be degraded by the cell to release the cytotoxic agent.

Hetero-bi-functional cross-linkers such as SPDP also can be used to conjugate the cytotoxic agent to the basement membrane binding agent, thereby creating a disulfide bond between the cytotoxic agent and the basement membrane binding agent. Once the resulting hybrid molecule is internalized by the retinal pigment epithelial cell, the disulfide bond is hydrolyzed to release the cytotoxic agent, thereby resulting in the destruction of the cell.

It is believed that recombinant DNA technology also can be used to construct the gene for a toxin with a basement membrane binding protein sequence incorporated therein. This gene may be expressed in a host cell and the product purified from the growth medium.

By way of example and not by way of limitation, a conjugate of polylysine and saporin was prepared by coupling polylysine to SPDP in accordance with the instructions stated by the manufacturer of the SPDP. The free SPDP was then removed using a filtration technique or, in the alternative, through the use of a sepharose heparin column. The resulting polylysine-SPDP was then reduced with dithiothreatol. Saporin was then coupled with SPDP in the same manner and added to the solution of polylysine-SPDP. The resulting solution filtered to remove uncoupled agents, thereby producing a conjugated polylysine-saporin solution.

The solution containing the basement membrane binding agent can comprise a variety of known biocompatible agents. In one embodiment of the present invention, the basement membrane binding agent is contained in a balanced salt solution. Solutions containing viscoelastics such as methylcellulose also can be used in connection with the present invention. It will be appreciated that other known biocompatible solutions can be used in connection with the method of the present invention.

Although the present invention has been described herein with respect to certain preferred embodiments, it will be appreciated by one of ordinary skill in the pertinent art that various modifications can be made without departing from the intended spirit and scope of the invention.

What is claimed is:

1. A method for destroying retinal pigment epithelial cells in a vitreous chamber of a phakic eye following vitrectomy and retina reattachment, said method comprising:

providing a solution comprising a heparin binding agent that binds to the basement membrane of said vitreous chamber conjugated to a cytotoxic agent;

introducing said solution into said vitreous chamber;

maintaining said solution in said vitreous chamber for a predetermined period of time sufficient for said heparin binding agent that binds to the basement membrane of said vitreous chamber to bind to a basement membrane within said vitreous chamber; and removing said solution from said vitreous chamber; whereby retinal pigment epithelial cells on said basement membrane within said vitreous chamber are exposed to said heparin binding agent that binds to the basement membrane of said vitreous chamber conjugated to a cytotoxic agent such that said retinal pigment epithelial cells are destroyed.

2. A method for destroying retinal pigment epithelial cells in a vitreous chamber of a phakic eye following vitrectomy and retina reattachment in accordance with claim 1, wherein said heparin binding agent that binds to the basement membrane of said vitreous chamber is selected from a group consisting of: polylysine, fibronectin, laminin, type IV collagen, thrombospondin, vitronectin, and platelet factor IV.

3. A method for destroying retinal pigment epithelial cells in a vitreous chamber following vitrectomy and retina reattachment in accordance with claim 2, wherein said heparin binding agent that binds to the basement membrane of said vitreous chamber is polylysine.

4. A method for destroying retinal pigment epithelial cells in a vitreous chamber following vitrectomy and retina reattachment in accordance with claim 1, wherein said cytotoxic agent is selected from a group consisting of: saporin, ricin, doxoribicin, mitoxanthrone, vinca alkaloids, vinblastine, colchicine, and cytochasins.

5. A method of destroying retinal pigment epithelial cells in a vitreous chamber following vitrectomy and retina reattachment in accordance with claim 4, wherein said cytotoxic agent is selected from a group consisting of saporin and ricin.

6. A method for destroying retinal pigment epithelial cells in a vitreous chamber following vitrectomy and retina reattachment in accordance with claim 4, wherein said cytotoxic agent is saporin.

7. A method for destroying retinal pigment epithelial cells in a vitreous chamber following vitrectomy and retina reattachment in accordance with claim 1, wherein said solution comprises a balanced salt solution.

8. A method for destroying retinal pigment epithelial cells in a vitreous chamber following vitrectomy and retina reattachment in accordance with claim 1, wherein said solution comprises a viscoelastic material.

9. A method for destroying retinal pigment epithelial cells in a vitreous chamber following vitrectomy and retina reattachment in accordance with claim 1, wherein said cytotoxic agent is conjugated to said heparin binding agent that binds to the basement membrane of said vitreous chamber using a water soluble carbodiimide technique.

10. A method for destroying retinal pigment epithelial cells in a vitreous chamber following vitrectomy and retina reattachment in accordance with claim 1, wherein said cytotoxic agent is conjugated to said heparin binding agent that binds to the basement membrane of said vitreous chamber using a hetero-bi-functional cross-linker.

11. A method for destroying retinal pigment epithelial cells in a vitreous chamber following vitrectomy and retina reattachment in accordance with claim 1, wherein said heparin binding agent that binds to the basement membrane of said vitreous chamber is polylysine and said cytotoxic agent is saporin.

* * * * *